(12) United States Patent
Van Schijndel et al.

(10) Patent No.: US 8,376,986 B2
(45) Date of Patent: Feb. 19, 2013

(54) BREAST PUMP FOR EXPRESSING MILK FROM A BREAST

(75) Inventors: Nicolle Hanneke Van Schijndel, Eindhoven (NL); Valery Stephanovich Kot, Eindhoven (NL); Ronaldus Maria Aarts, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 73 days.

(21) Appl. No.: 12/808,690

(22) PCT Filed: Dec. 12, 2008

(86) PCT No.: PCT/IB2008/055241
§ 371 (c)(1),
(2), (4) Date: Jun. 17, 2010

(87) PCT Pub. No.: WO2009/081313
PCT Pub. Date: Jul. 2, 2009

(65) Prior Publication Data
US 2011/0004154 A1    Jan. 6, 2011

(30) Foreign Application Priority Data
Dec. 21, 2007    (EP) .................................... 07123891

(51) Int. Cl.
*A61M 1/06*    (2006.01)
(52) U.S. Cl. ............................................ 604/74; 604/76
(58) Field of Classification Search .................... 604/74, 604/76
See application file for complete search history.

(56) References Cited

U.S. PATENT DOCUMENTS

| 4,064,838 | A | 12/1977 | Mukarovsky et al. |
| 5,571,084 | A | 11/1996 | Palmer |
| 6,547,756 | B1 | 4/2003 | Greter et al. |
| 6,673,036 | B1 | 1/2004 | Britto |
| 7,201,735 | B2 | 4/2007 | Atkin et al. |
| 2005/0228342 | A1 | 10/2005 | Yuen |
| 2008/0177224 | A1 * | 7/2008 | Kelly et al. ............... 604/74 |

FOREIGN PATENT DOCUMENTS

| EP | 1430918 A | 6/2004 |
| GB | 2435617 A | 9/2007 |
| WO | 0057934 A1 | 10/2000 |
| WO | 03028616 A2 | 4/2003 |

* cited by examiner

*Primary Examiner* — Quynh-Nhu H Vu

(57) ABSTRACT

Breast pump for expressing milk from a breast, comprising at least one breast cup (2) for receiving a breast, a pumping system (10) in fluid connection (11) with the at least one breast cup (2) for applying a negative pressure on said breast and a detection unit (3) comprising at least one sensor for measuring a parameter during use of the breast pump (1), wherein the breast pump (1) is adapted for optimising breast pump settings by actively controlling at least one breast pump pumping property, based on measurements of the at least one sensor (4, 5), during a period of use of the breast pump (1), in order to personalize operation of said breast pump (1) for a particular user.

17 Claims, 2 Drawing Sheets

BREAST PUMP FOR EXPRESSING MILK FROM A BREAST

FIELD OF THE INVENTION

The invention relates to a breast pump for expressing milk from a breast, comprising at least one breast cup for receiving a breast, a pumping system in fluid connection with the at least one breast cup for applying a negative pressure on said breast and a detection unit comprising at least one sensor for measuring a parameter during use of the breast pump.

BACKGROUND OF THE INVENTION

Breast pumps are devices used for expression of milk from a woman's breast, for instance if the baby is not able to extract the milk itself for different reasons for instance due to suckling problems or when the mother is separated from the baby. Also other reasons, like excessive milk production or breast problems or injuries may result in the woman using a breast pump instead of breast feeding the baby. Different kinds of breast pumps exist, such as manually driven or electrically driven. The known breast pumps have different disadvantages. For instance, a manually driven breast pump requires a lot of manual work to apply a desired suction frequency and a desired suction power. This may result in a time consuming operation. In order to ease the expression of milk, electrically driven breast pumps are available, which breast pumps replace the manual operation by an electrically driven pumping operation. The user of the breast pump only needs to control the settings of the breast pump, by for instance controlling the frequency of suction cycles and/or suction power. However, in practice it is not easy for a user to control the settings in an intended manner, thereby risking wrong use of the breast pump resulting in an efficiency reduction of the pump or even damaging the breast tissue. In fact, such problems can actually result in giving up breast feeding completely. This is not desired, since it is known that breast feeding a baby contributes to the baby's health.

An improved breast pump, trying to guide the user in applying the proper breast pump settings, is for instance disclosed in US 2005/0028342. The known breast pump comprises a milk flow sensor that measures the milk flow during the milk expression cycle. In dependence of the measured milk flow, the breast pump is able to switch between different pumping settings. However, such a breast pump does not take into account that before and after the actual milk expression, there is no milk flow or a minimum milk flow. Therefore, during the period before and after the actual milk expression, the user cannot be properly guided in applying the proper settings during the period of use of the breast pump. It is therefore an object of the invention, to provide an improved breast pump that takes into account the period before and after the actual milk expression. More particular, it is an object of the invention to provide an improved breast pump that works efficient during the period of use of the breast pump and at the same time is easy-to-use.

SUMMARY OF THE INVENTION

To that end, an apparatus according to the invention is characterized in that the breast pump is adapted for optimising breast pump settings by actively controlling at least one breast pump pumping property, based on measurements of the at least one sensor, during a period of use of the breast pump, in order to personalise operation of said breast pump for a particular user. Because the breast pump is able to optimise breast pump settings based on measurements of the at least one sensor during the period of use of the breast pump, thus also before actual milk expression starts and after the milk expression decreases or ends, a breast pump that is adapted to personal characteristics of a particular user is provided. Such a breast pump provides the best settings by actively controlling at least one breast pump pumping property, based on measurements of the at least one sensor for said user during each stage of the actual period of use of the breast pump, in an easy manner without hurting the user and at the same time providing increased expressed milk quantity, milk quality and/or increased pumping efficiency. Thus, also during the period before the actual milk expression starts, the at least one pumping property is measured and based thereon, the pumping property may be actively controlled. In case the measured value does not comply with the desired value, the pumping property is actively controlled or adapted. The breast pump pumping property may for instance be the pumping power and/or the pumping frequency. It is clear that the at least one pumping property may be actively controlled during an entire period of use of the breast pump. But it is also possible that the at least one pumping property may be actively controlled during one or more parts of the entire period of use of the breast pump, for instance only during the period before the actual milk expression starts. Consequently, the accessibility to use said breast pump is increased considerably.

It may be advantageous, according to a further elaboration of the invention, that the at least one sensor is a pressure sensor adapted for measuring the negative pressure in the at least one breast cup, preferably in at least a space between said breast cup and the breast, during said period of use of the breast pump. Thanks to said pressure sensor it is possible to measure the pressure that is actually applied to the breast. The actual applied negative pressure on the breast depends on the suction power of the pumping system, but also on the other conditions, for example air leakage between the breast and the breast cup or on other locations in the fluid connection between the pumping system and the breast cup, or the amount of air in the cup. This may be different for every user, since the breast shape of each user and the way that the breast cup covers said breast can be different. By measuring the actual negative pressure applied to the breast during use of the breast pump, the user does not have to find out and try which are the optimal settings of the breast pump. Furthermore, it prevents damaging the delicate breast tissue, since it is clear, and not blurred by other factors, what amount of pressure is applied to the breast. Since a negative pressure is applied during the period of use of the breast pump, even before the milk flows, the user can be guided in applying the proper settings during said period of use. This results in an easy-to-use breast pump, even for inexperienced users.

Preferably, according to a further elaboration of the invention, the pressure sensor is an air pressure sensor that is adapted to detect a minimum negative pressure and/or a maximum negative pressure in at least the breast cup. This enables that the user can be warned in case the applied pressure is too high in the suction phase (maximum pressure) or in case that the release pressure (minimum pressure) is too high during the release phase. It is noted that during a period of use of the breast pump, the pumping system operates with suction cycles comprising alternate suction and release phases. When the pressure is too high, more air can be introduced in the breast cup, or at least in the space between the breast cup and the breast, in order to reduce the pressure. The pressure sensor may in this case also function as a safety valve that opens automatically when the pressure is too high.

In a further advantageous embodiment of the invention, the detection unit comprises at least a milk flow sensor that is adapted to measure milk output as a function of time and/or its average value over at least a few previous performed suction cycles. For instance, by measuring the applied negative pressure during a suction cycle and at the same time measuring the milk flow during said suction cycle, the efficiency of the breast pump can be further increased. By measuring the milk flow and analysing said milk flow in relation to the applied pressure, the settings of the breast pump can even better be determined.

According to another aspect of the invention, the detection unit comprises at least a sensor that is adapted for assessing at least one property of at least one biological particle of extracted milk. Such a sensor according to another aspect of the invention may comprise an electromagnetic sensor, a physical sensor, a biological sensor and/or the like. For instance, it is known that the electromagnetic properties of the milk are influenced by different parameters, for instance relating to the woman's health or to the milk quality. For example, in case of the occurrence of mastitis, the electrical conductivity of the milk will be increased. Conductivity of the milk can be measured by an electromagnetic sensor. It is also possible to measure density of the milk with aid of a physical sensor, to measure pH level with aid of a chemical sensor, to count cells with aid of a biological sensor or to measure other properties with other known sensors. Such determined information can be helpful to prevent or cure health problems and further optimise milk extraction parameters and increase extracted milk quantity and milk quality. It is possible that the milk flow sensor and said sensor adapted for assessing at least one property of at least one biological particle of extracted milk are combined in the same sensor.

In yet another embodiment of the invention, the pressure sensor may be provided in a pump body of the pumping system, in the fluid connection between the pumping system and the breast cup and/or in the breast cup. The pressure sensor can be placed in any of the mentioned locations as long as it is able to determine the actual applied pressure on the breast. A milk flow sensor and/or a sensor to measure the electromagnetic properties may be placed nearby or in the milk flow.

The breast pump may, according to another aspect of the invention, comprise a control unit adapted to analyse data output from the detection unit based on said sensor measurements. After analysing said data output, thus for instance the applied pressure at a certain moment and/or the milk flow at a certain moment, which data output is provided by the at least one sensor, the control unit may suggest a change in the settings of the breast pump.

According to a further elaboration of the invention, the control unit may then control the pumping system in dependence of the data output, for instance by adapting the pumping power and/or the pumping frequency in order to optimize the milk extraction and usage comfort.

It is also possible that the control unit may be adapted to provide information to a user of the breast pump in dependence of the data output. The control unit may suggest a value for the pumping power and/or the pumping frequency. The user does not have to try different settings, but has just to set the suggested values in order to optimise the milk extraction and the usage comfort. The user may also change pumping settings dependent on perceived comfort.

According to a further aspect of the invention, the control unit may be adapted to control the pumping system during the period of use of the breast pump according to a predetermined pumping cycle providing predetermined frequency values and pressure values in time. This enables the pumping system to change the pumping power and the pumping frequency according to the course of the predetermined pumping cycle. Of course, the values may be adapted during the period of use of the breast pump in dependence of the actual measured pressure and/or milk flow value.

In a further elaboration of the invention, the control unit may be adapted to store data based on the sensor measurements, wherein in use the control unit provides breast pump settings based on the stored data. This provides a control unit having a learning mechanism. This allows a predetermined pumping cycle to be optimised for the user of the breast pump, such that during the next actual period of use of the breast pump the pressure and the frequency may be more optimised for that user. Since for each woman the optimal pumping cycle may be different, it allows the breast pump to be personalized. It may also be possible to adapt the pumping cycle according to a user's personal wishes or according to an expert advice.

Further advantageous embodiments of a breast pump according to the present invention are set forth in the dependent claims.

BRIEF DESCRIPTION OF THE DRAWINGS

To explain the invention, exemplary embodiments thereof will hereinafter be described with reference to the accompanying drawings, wherein.

DETAILED DESCRIPTION OF EMBODIMENTS

Figure 1:
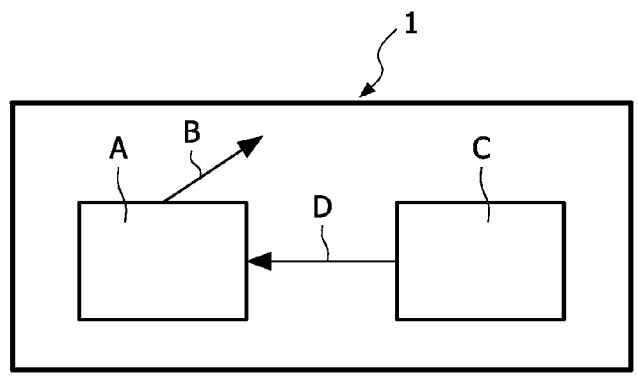
FIG. 1 schematically shows the working principle of the breast pump according to the invention.

FIG. 1 shows the working principle of the breast pump 1 according to the invention. Block A represents determining the required settings of the breast pump 1 on a certain moment during the period of use of the breast pump 1, for instance just after starting the breast pump 1. The breast pump 1 is driven to operate with a certain pumping frequency and pumping power, represented by arrow B. Block C represents the measurement of the actual parameters of the entire system, for example maximum negative pressure in the breast shield 2 (see FIG. 3), or at least in the space between the breast shield 2 (see FIG. 3) and the breast, and of the actual milk flow at that moment. After measuring the pressure and the milk flow, the data is transmitted back (represented by arrow D) and is analysed (also represented by block A). According to the analysed data, adapting of the breast pump settings may be suggested, which may be done automatically or manually by the user according to the suggested values. Thus, the breast pump 1 is adapted for optimising the breast pump settings by actively controlling a breast pump pumping property, for instance pumping power or pumping frequency based on measurements of one or more sensors, during a period of use of the breast pump 1. Consequently, operation of the breast pump 1 may be personalised for a particular user. It is noted that a period of use of the breast pump 1 comprises the entirety of suction cycles from the start of the breast pump operation till the end of breast pump operation, thus also including the period before the actual milk extraction from the breast and the period after the actual milk extraction from the breast. Furthermore, the pumping cycle is defined as the entirety of pumping property values during an entire period of use of the breast pump 1. The values of the pumping cycle may be varied during the period of use of the breast pump, as will be discussed at FIG. 2.

Figure 2:
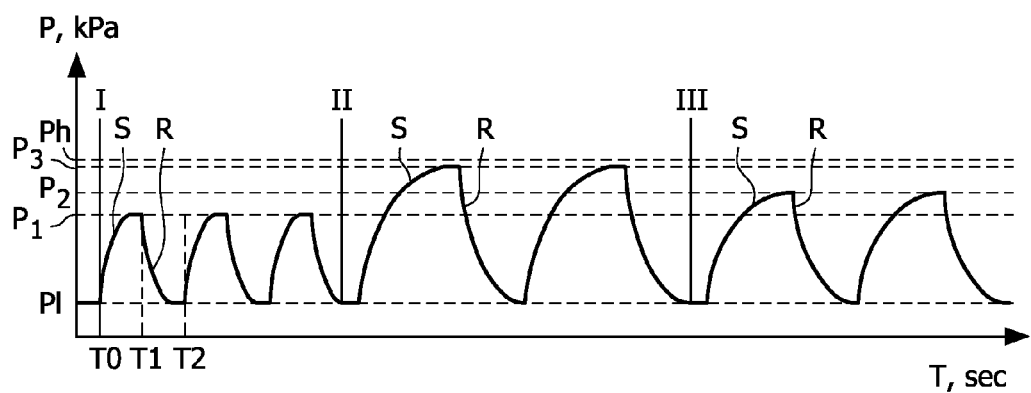
FIG. 2 schematically shows a pumping cycle of a the breast pump according to the invention.

In FIG. 2, several suction cycles of the breast pump 1 during the period of use of the breast pump 1 according to the invention are schematically shown. As can be seen, the pumping cycle comprises three different stages I, II, III, wherein the respective suction cycles are different, each stage comprising a predetermined pumping frequency and predetermined negative pressure. A suction cycle furthermore consists of two phases S, R that are repeated alternately during all stages I, II, III of the period of use of the breast pump 1. The two phases comprise a suction phase S and a release phase R. During the suction phase S, milk is supposed to flow from the breast and during the release phase R, the milk is collected in a receiving element (not shown) that may be in fluid connection to the breast cup 2 (see FIG. 3) for receiving extracted milk from the breast. Such a receiving element may for instance be a baby bottle that is connected to the breast pump 1. The suction phase S starts at moment T0 by increasing the negative pressure on the breast, thus increasing the vacuum level under the breast cup from the release pressure P1 to a desired pressure according to the stage of the pumping cycle. The negative pressure is kept at the desired value until moment T1. Then the suction phase S ends and the release phase R starts. The negative pressure will decrease until it reaches the P1 value and stays at that value until moment T2, wherein the suction phase S starts again. The suction phases S and the release phases R are repeated alternately during the pumping cycle. Depending on the stage of said cycle, a certain frequency and a desired maximum pressure will be provided by the breast pump 1, as will be discussed later on. The suction cycle time Tc for the suction phase S and the release phase R is represented by Tc=T2−T0. The suction frequency F is determined by F=1/Tc. During each suction cycle a certain amount of milk is extracted.

As is mentioned above, the pumping cycle comprises three different stages that are adapted to the milk expression process from the breast in order to provide efficient removal of the milk.

The first stage I, being the stimulation stage, may require the pumping system 10 (see FIG. 3) to operate with a relatively high pumping frequency F, of for instance about 1.5 Hz, and a relatively low pressure $P_1$, of for instance about 15 kPa. In this stage I, the breast is stimulated to start expressing milk using the milk ejection reflex.

The second stage II, being the milking stage, may require the pumping system 10 to operate with a relatively low pumping frequency F, preferably a frequency of about 0.75 Hz, and a relatively high pressure $P_3$, for instance about 30 kPa. At this stage II, a large amount of milk will be extracted from the breast.

The third stage III, being the stripping stage, may require a relatively low pumping frequency F, of for example 0.75 Hz and a medium pressure $P_2$, for instance about 20 kPa. In this stage, almost all milk is already extracted from the breast, but the remaining milk that is considered to be very nutritious, still has to be expressed. This last part of the expression is also desirable for physiological reasons, for instance to prevent milk stasis. The last part of the expression of the milk has to be done carefully in order to prevent breast injuries.

Figure 3:
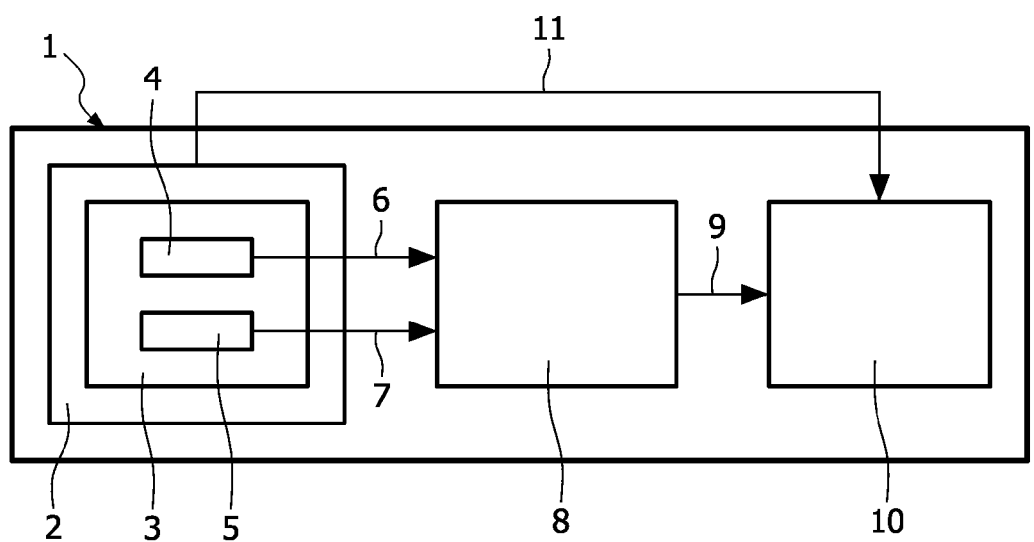
FIG. 3 schematically shows a first embodiment of the breast pump.

FIG. 3 schematically shows a first embodiment of the breast pump 1. The breast pump 1 comprises at least one breast cup 2 for receiving a breast. It is noted that the breast cup may be a flexible cup, a hood or a shield, which may even be less flexible. Also other kinds of breast cups or the like can be used. The breast pump 1 further comprises a pumping system 10 in fluid connection 11 with the breast cup 2 for applying a negative pressure on said breast in the breast cup 2 by removing air from the breast cup 2, more specific from at least the space between the breast cup 2 and the breast of the user. The breast pump 1 further comprises a detection unit 3 having a pressure sensor 4 and a milk flow sensor 5. It also may be possible, in another embodiment of the invention, that the detection unit 3 only comprises a pressure sensor 4 as described before. Furthermore, an additional sensor for assessing at least one property of at least one biological particle of extracted milk (not shown) may be provided. Such a sensor can be an electromagnetic sensor for measuring conductivity of the expressed milk, a physical sensor for measuring, for instance, density of the milk, a chemical sensor for measuring, for instance a pH level of the milk, a biological sensor for instance for counting cells. Of course said sensor can be another sensor capable of assessing another property of a biological particle of the extracted milk. The pressure sensor 4 is adapted to measure a negative pressure in the breast cup 2, preferably in at least a space between the breast cup 2 and the breast, during a period of use of the breast pump 1. The milk flow sensor 5 is adapted to measure milk flow output as a function of time and/or its average value over at least a few previously performed suction cycles. The pressure sensor may be provided in a pump body (not shown) of the pumping system 10, in the fluid connection 11 between the breast cup 2 and the pumping system 10 or in the breast cup 2 itself. It is also possible to use more sensors that are provided on different locations in the breast pump 1. The milk flow sensor 5 may be provided in or near the milk flow from the breast and may also be arranged to measure the total amount of expressed milk.

The breast pump 1 comprises a control unit 8 that is adapted to analyse data output (represented by arrow 6 and arrow 7) from the detection unit 3. The control unit 8 is also adapted to control the pumping system 10 in dependence of the data output, for instance by adapting the pumping power and/or the pumping frequency. In another embodiment it also may be possible that the control unit 8 is adapted to provide information about the measured and analysed data to a user of the breast pump 1 in dependence of the data output. Such information may for instance be provided on a display. The user can, according to the provided information, change the settings of the pumping system 10 in order to increase efficiency of the pumping system 10. Also additional information may be provided, such as the total amount of milk already expressed. However, in the embodiment of the breast pump 1 that is shown in FIG. 3, the control unit 8 is adapted to control the pumping system 10 by automatically adapting the settings (represented by arrow 9).

In use, the settings of the pumping system 10 are adjusted according to the stages of the pumping cycle as shown in FIG. 2. During the stimulation stage I, the control unit 8 controls the pumping system 10 to perform suction cycles with a relatively high frequency F and a relatively low pressure $P_1$. If the actual pressure, measured by the pressure sensor 4, differs from the predetermined pressure $P_1$ by more than a certain threshold, the control unit 8 adjust the settings of the pumping system 10 accordingly. If the measured minimum pressure P1 (see FIG. 2) at the end of the release phase R is higher than 0 by more than a certain threshold, the control unit 8 adjusts the ratio between the suction phase S and the release phase R by allowing more air from outside of the breast cup 2 to enter the breast cup 2, the fluid connection 11 and the pumping system 10. A minimum pressure P1 that may be too high, may result in an inefficient stimulation of the breast and it may also prevent milk from leaving the breast cup 2 to enter the receiving element, but may instead be forced into the pumping system 10 which leads to unwanted effects. It may also be possible to interrupt the pumping cycle to allow air in the breast cup 2 or in the pumping system 10. Therefore, a special valve that is controlled by the control unit 8 may be provided. When the milk flow sensor 5 measures a certain milk flow, i.e. the instantaneous milk gain is higher than a predetermined threshold, the sensor 5 informs the control unit 8 that the milk extraction has started. At that moment, the control unit 8 controls the pumping system 10 to change the pumping settings in order to enter stage II of the pumping cycle. In the milking stage II, the control unit 8 controls the pumping system 10 to perform suction cycles with a relatively low frequency and a relatively high pressure $P_3$, as described at FIG. 2. The frequency F can be adapted on the instantaneous milk gain if necessary. The suction phase S will not change into the release phase R until the milk flow has dropped below a certain predetermined threshold. The milking stage II will end at the moment that the milk flow sensor 5 informs the control unit 8 that the average value of the instantaneous milk gain over the last couple of suction cycles has dropped below a predetermined threshold.

After stage II has ended, the stripping stage III starts when almost all milk is extracted from the breast. It is also important to extract the remaining milk from the breast, as the remaining milk is very nutritious. Furthermore, the extraction of the remaining milk is very advantageous in preventing milk stasis. The stripping stage III needs to be done carefully, since "dry milking" can lead to breast problems, such as nipple problems. At this stage III, the control unit 8 controls the pumping system 10 to perform suction cycles with a relatively low frequency, as described at FIG. 2, and a medium pressure $P_2$. The stripping stage III ends when the instantaneous milk gain is zero or is close to zero over a predetermined time period.

In the above described embodiment, certain predetermined pressure and instantaneous milk gain thresholds are mentioned. It is clear that such thresholds may differ from woman to woman. It may therefore be advantageous that the control unit 8 can adapt the pumping cycle as described in FIG. 2 to specific user settings. With every new actual period of use of the breast pump 1, it will be a little bit more optimised. The predetermined pumping cycle may also be further optimised by adapting it to a user's feedback or on basis of an advice from an expert. In another embodiment of the invention, the predetermined pumping cycle may be adapted to mimic the suction behaviour of a particular baby. Furthermore, it may be advantageous if the desired maximum pressure during the actual period of use of the breast pump 1 stays in the range of 150-250 mm Hg (approximately 20-33 kPa). Values below the range may be ineffective at expressing milk and values above said range may cause pain.

In yet another embodiment of the invention, the breast pump 2 may comprise two breast cups 2 to attach simultaneously to both breasts of a user. The detection unit 3 can be adapted to measure parameters such as negative pressure and milk flow in both breast cups 2 independently. The control unit 8 may control the pumping system 10 to apply a pumping power and pumping frequency to both breasts in a jointly optimal way. In another embodiment, it is also possible that each breast cup 2 is in fluid connection with an independent controllable pumping system 10, in order to provide the optimal settings for each breast independently. The breast pump 1 may therefore also comprise two pumping systems.

It should be understood, that it is possible to control the pumping system 10 in any desired way, for example in order to pump with a constant frequency, for instance not dependent on the instantaneous milk gain. It is also possible that the control unit 8 may switch between the stages I, II, III on a desired moment, or for instance according to measured parameters. It may be possible that during stage III the instantaneous milk gain increases. The control unit 8 may react by controlling the pumping system 10 to return to the settings that are used during stage II. The control unit 8 may be adapted to control the pumping system 10 such that a change in pumping power and/or pumping frequency may not be reached in an instant moment but during a transition period of a certain time period, for instance in a few seconds. Also other changes in the controlling of the pumping system 10 may be dependent on passed time periods. Furthermore, it is possible to connect the breast pump 1 to a system that transfers measured parameters to another remote location. For instance, an expert may via the internet be informed about the measured parameters and give feedback to the control unit 8 of the breast pump 1 or to the user of the breast pump 1. The measure parameters may also be stored in the control unit 8, such that they can be consulted later.

The invention is not in any way limited to the exemplary embodiments presented in the description and drawings. All combinations (of parts) of the embodiments shown and described are explicitly understood to be incorporated within this description and are explicitly understood to fall within the scope of the invention. Moreover, many variations are possible within the scope of the invention, as outlined by the claims. Furthermore, any reference signs in the claims shall not be construed as limiting the scope of the invention.

The invention claimed is:

1. Breast pump for expressing milk from a breast, comprising:
    at least one breast cup for receiving a breast,
    a pumping system in fluid connection with the at least one breast cup for applying a negative pressure on said breast and a detection unit comprising at least one sensor for measuring a parameter during use of the breast pump; and
    a controller which progressively optimizes settings of the pumping system with each use of the breast pump for a particular user based on measurements of the at least one sensor,
    wherein the controller automatically optimizes breast pump settings by actively controlling at least one of a breast pumping power and a breast pumping frequency to personalize operation of said breast pump for the particular user.

2. Breast pump according to claim 1, wherein the at least one sensor is a pressure sensor adapted for measuring the negative pressure in the at least one breast cup.

3. Breast pump according to claim 2, wherein the pressure sensor is an air pressure sensor that is adapted to detect a minimum negative pressure and/or a maximum negative pressure in at least the breast cup.

4. Breast pump according to claim 2, wherein the at least one sensor is a pressure sensor adapted for measuring the negative pressure in a space between the breast cup and the breast, during the period of use of the breast pump.

5. Breast pump according to claim 1, wherein the detection unit comprises at least a milk flow sensor that is adapted to measure milk flow output as a function of time and/or its average value over at least a few previous performed suction cycles.

6. Breast pump according to claim 1, wherein the detection unit comprises at least a sensor that is adapted for assessing at least one property of at least one biological particle of extracted milk.

7. Breast pump according to claim 6, wherein said sensor for assessing at least one property of at least one biological particle of extracted milk comprises an electromagnetic sensor, a physical sensor, and/or a biological sensor.

8. Breast pump according to claim 1, wherein the pressure sensor is provided in a pump body of the pumping system, in the fluid connection between the pumping system and the breast cup and/or in the breast cup.

9. Breast pump according to claim 1, wherein the control unit is adapted to analyze data output from the detection unit based on said sensor measurements.

10. Breast pump according to claim 9, wherein the control unit is adapted to control the pumping system in dependence of the data output by adapting the pumping power and/or the pumping frequency.

11. Breast pump according to claim 9, wherein the control unit is adapted to provide information to a user of the breast pump in dependence of the data output.

12. Breast pump according to claim 9, wherein the control unit is adapted to control the pumping system during the period of use of the breast pump according to a predetermined pumping cycle providing predetermined frequency values and pressure values in time.

13. Breast pump according to claim 12, wherein the predetermined pumping cycle comprises a first stage with a high frequency of 1.5 Hz, and a low pressure of 15 kPa.

14. Breast pump according to claim 12, wherein the predetermined pumping cycle comprises a second stage with a low frequency of 0.75 Hz, and a high pressure of 30 kPa.

15. Breast pump according to claim 12, wherein the predetermined pumping cycle comprise a third stage with a low frequency of 0.75 Hz, and a medium pressure of 20 kPa.

16. Breast pump according to claim 9, wherein the control unit is adapted to store data based on the sensor measurements, wherein in use the control unit provides breast pump settings based on the stored data.

17. Breast pump according to claim 1, wherein the detection unit is adapted to measure parameters for more than one breast, wherein the control unit is adapted to control the pumping system for both breast cups independently.

* * * * *